US008840643B2

(12) United States Patent
Dreyfuss

(10) Patent No.: US 8,840,643 B2
(45) Date of Patent: Sep. 23, 2014

(54) SEGMENTED SUTURE ANCHOR

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 489 days.

(21) Appl. No.: 12/824,558

(22) Filed: Jun. 28, 2010

(65) Prior Publication Data

US 2011/0004243 A1    Jan. 6, 2011

Related U.S. Application Data

(60) Provisional application No. 61/222,740, filed on Jul. 2, 2009.

(51) Int. Cl.
*A61B 17/04* (2006.01)
*A61B 17/00* (2006.01)

(52) U.S. Cl.
CPC ... *A61B 17/0401* (2013.01); *A61B 2017/00867* (2013.01); *A61B 2017/0438* (2013.01); *A61B 2017/0414* (2013.01)
USPC .......................................... 606/232; 606/300

(58) Field of Classification Search
USPC ....................................................... 606/232
See application file for complete search history.

(56) References Cited

U.S. PATENT DOCUMENTS

| 5,324,308 | A  | * | 6/1994  | Pierce ............................ 606/232 |
| 5,405,359 | A  | * | 4/1995  | Pierce ............................ 606/232 |
| 5,718,717 | A  | * | 2/1998  | Bonutti ........................... 606/232 |
| 5,897,574 | A  | * | 4/1999  | Bonutti ........................... 606/232 |
| 5,964,783 | A  | * | 10/1999 | Grafton et al. .................. 606/232 |
| 6,156,056 | A  | * | 12/2000 | Kearns et al. ................... 606/232 |
| 6,500,195 | B2 | * | 12/2002 | Bonutti ........................... 606/232 |
| 6,923,824 | B2 | * | 8/2005  | Morgan et al. .................. 606/232 |
| 7,226,469 | B2 | * | 6/2007  | Benavitz et al. ................ 606/232 |
| 7,658,750 | B2 | * | 2/2010  | Li .................................... 606/232 |
| 7,850,714 | B2 | * | 12/2010 | Rotella et al. ................... 606/232 |
| 2002/0087190 | A1 | * | 7/2002 | Benavitz et al. ................ 606/232 |
| 2005/0228448 | A1 | * | 10/2005 | Li .................................... 606/232 |
| 2007/0073299 | A1 | * | 3/2007 | Dreyfuss et al. ................ 606/72 |
| 2007/0150003 | A1 | * | 6/2007 | Dreyfuss et al. ................ 606/232 |
| 2007/0225764 | A1 | * | 9/2007 | Benavitz et al. ................ 606/232 |
| 2008/0058816 | A1 | * | 3/2008 | Philippon et al. ............... 606/72 |
| 2008/0147102 | A1 | * | 6/2008 | Rotella et al. ................... 606/154 |
| 2009/0149883 | A1 | * | 6/2009 | Brunsvold ....................... 606/232 |
| 2009/0192545 | A1 | * | 7/2009 | Workman ........................ 606/232 |
| 2012/0078300 | A1 | * | 3/2012 | Mayer et al. .................... 606/232 |

* cited by examiner

*Primary Examiner* — Melanie Tyson
*Assistant Examiner* — Todd J Scherbel
(74) *Attorney, Agent, or Firm* — Dickstein Shapiro LLP

(57) ABSTRACT

A segmented suture anchor for fixation of soft tissue to bone. The segmented suture anchor is formed of multiple body segments that allow the suture anchor to be inserted and passed through a curved instrument such as a curved cannulated guide. At least two of the multiple body segments are connected by a strand of material (for example, a flexible suture strand, a suture tape, nitinol strand, or high-strength suture). The strand of material may be attached to the anchor by a connecting region (for example, a bonded or knotted region). The strand of material may also form a closed loop or eyelet attached to the suture anchor, to allow additional suture strands to be loaded through the closed loop or eyelet and aid in the fixation of soft tissue.

4 Claims, 1 Drawing Sheet

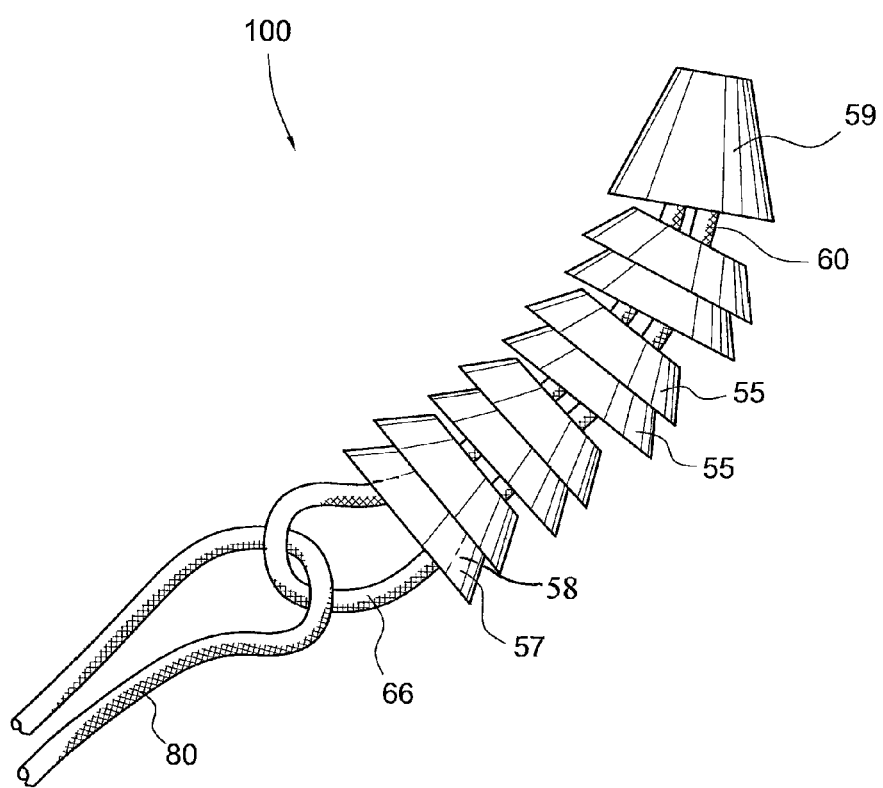

SEGMENTED SUTURE ANCHOR

CROSS-REFERENCE TO RELATED APPLICATIONS

This application claims the benefit of U.S. Provisional Application Ser. No. 61/222,740, filed Jul. 2, 2009, the entire disclosure of which is incorporated by reference herein.

FIELD OF THE INVENTION

The present invention relates to the field of surgery reconstruction and, more particularly, to suture anchors for reattaching soft tissue to bone.

BACKGROUND OF THE INVENTION

When soft tissues such as tendons or ligaments detach from bone, it is often necessary to reconnect the structures surgically. Techniques and devices that have been developed generally involve tying the soft tissue with suture to an anchor or a hole provided in the bone tissue. Reattachment with suture involves knot-tying, which can present difficulties especially when operating on small joints, such as those in the hand and wrist.

In addition, certain applications requiring attachment of soft tissue necessitate insertion and passing of suture anchors through curved instruments (for example, curved inserters or curved cannulated guides). Suture anchors which have been developed for such applications are either very short or purposely undersized to allow passage through the curved instruments.

Accordingly, there is a need for a suture anchor that has as much strength as a conventional anchor and yet allows easy insertion and passage through a curved instrument. Also needed is a suture anchor that can be easily passed through either a curved or straight instrument, and that can be employed for reattaching tissue torn from bone using minimal knot tying.

SUMMARY OF THE INVENTION

The present invention provides techniques and suture anchors for ligament repair and fixation, including soft tissue to bone. The suture anchor of the present invention comprises multiple body segments that allow the suture anchor to be inserted and passed through a curved instrument such as a curved cannulated guide. At least two of the multiple body segments are connected by a strand of material (for example, a flexible suture strand, a suture tape, nitinol strand, or high-strength suture such as FiberWire® suture, among many others). The strand of material may be attached to the anchor by a connecting region (for example, a bonded or knotted region). The strand of material may also form a closed loop or eyelet attached to the suture anchor, to allow additional suture strands to be loaded through the closed loop or eyelet and aid in the fixation of soft tissue.

These and other features and advantages of the invention will be more apparent from the following detailed description that is provided in connection with the accompanying drawing and illustrated exemplary embodiments of the invention.

BRIEF DESCRIPTION OF THE DRAWING

FIG. 1 illustrates a segmented suture anchor according to an exemplary embodiment of the present invention.

DETAILED DESCRIPTION OF THE PREFERRED EMBODIMENTS

The present invention provides a suture anchor with multiple body segments that allow the suture anchor to be inserted and passed through a curved instrument such as a curved cannulated guide. At least two of the multiple body segments (and preferably all) are connected by a strand of material (for example, a flexible suture strand, a suture tape, nitinol strand, or high-strength suture such as FiberWire® suture, among many others). The strand of material may be attached to the anchor by a connecting region (a bonded or knotted region). The strand of material connecting the anchor segments may also form a closed loop or eyelet of flexible material attached to the suture anchor, to allow additional suture strands to be loaded through the closed loop or eyelet and aid in the fixation of soft tissue.

The present invention also provides a method of soft tissue repair including fixation of soft tissue to bone. The method of the present invention comprises the steps of: (i) providing a pilot hole through bone; (ii) providing, in the vicinity of the pilot hole, a segmented suture anchor with multiple body segments, at least two of the body segments being connected by a material strand; (iii) attaching the suture anchor to soft tissue to be attached to bone; and (iv) passing the suture anchor through a straight or curved instrument, to insert the suture anchor into the pilot hole. The fixation of the segmented suture anchor by the method of the present invention is similar to the fixation of a one-piece suture anchor.

Referring now to the drawing, where like elements are designated by like reference numerals, FIG. 1 illustrates a segmented suture anchor 100 of the present invention comprising a body 50 formed of a plurality of body segments 55 attached by a strand of material 60.

In an exemplary embodiment only, body 50 includes tapered body segments 55 in the form of ribs 55, terminating in a blunt or rounded distal end 59. The proximal end 57 of the suture anchor body 50 preferably has a round, tapered drive head 58 which may be received in a recess of a hand driver. Body segments 55 allow segmented anchor 100 to be driven through a curved cannulated guide when inserted into bone (for example, when inserted into a pilot hole in a bone, for fixation of soft tissue to bone). In an exemplary embodiment, body segments 55 are disposed circumferentially at least partially around and partially along the length of strand 60. Body segments 55 are preferably provided serially along the length of strand 60 and in multiple pairs (for example, in a 2 segment-pair series). Body segments 55 have a truncated, conical shape, each segment increasing in diameter toward the head of the anchor. Body segments 55 may be formed of a bioabsorbable material such as poly(l-lactide-co-d,l-lactide) 70:30 (PLDLA), PEEK, metals or metal alloys (such as stainless steel, titanium or titanium alloys, for example), absorbable and/or nonaborbable materials, natural and/or synthetic polymers, among many others.

Although body segments 55 of suture anchor 100 have been illustrated as having a tapered shape (in the form of ribs, terminating in a blunt or rounded distal end), the invention is not limited to this exemplary only embodiment and contemplates individual body segments having different shapes and geometries, or a combination of different shapes and geometries. The individual segments may be also configured to interlock (snap fit) once driven along the suture and implanted. Alternatively, the shape of the last block/segment may be different from the shape of the remaining segments, and/or the last block/segment may be self-punching, for example.

In yet additional embodiments, the invention also contemplates a suture anchor with middle segments that may be cannulated with one or more holes for the suture to pass through and back around. The individual segments of the present invention may also be offered in different lengths to create the desired size of the anchor. The surgeon or medical personnel could pick the segments he/she wants and assemble the anchor before or during the surgical procedure.

The strand 60 preferably extends through the entire length of the anchor 100 and exits at the proximal end 57 of the anchor. In a preferred embodiment of the invention, strand 60 forms a loop or eyelet 66 outside the proximal end 57 of the anchor. Closed loop or eyelet 66 of the strand 60 allows additional suture strands to be loaded through the closed loop or eyelet, and aid in the fixation of soft tissue. For example, FIG. 1 illustrates only one suture strand 80 loaded through the closed loop or eyelet 66; however, the invention contemplates embodiments wherein a plurality of additional strands may be loaded through the closed loop or eyelet 66.

Strand 60 connecting segments 55 may be formed of a flexible strand such as a suture strand (any known type of suture selected according to the size of the anchor and the anticipated application). If a suture strand is employed, the suture may be a No. 2 polyester braided suture. In another exemplary embodiment, high-strength suture may be utilized, such as the high strength suture sold by Arthrex, Inc. of Naples, Fla. under the tradename FiberWire®, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. The suture may optionally include filaments of various colors.

Strand 60 may be also formed of suture tape (for example, a collagen stuffed suture tape) or nitinol, or combination of suture and tape, a stiff material, or combination of stiff and flexible materials, depending on the intended application. In an exemplary embodiment only, strand 60 may be a FiberTape® (as disclosed in U.S. Patent Publication No. 2005/0192631, the disclosure of which is incorporated in its entirety by reference herein).

Strand 60 may also contain collagen and/or strands of a high strength suture material such as Arthrex FiberWire®. Strand 60 of the segmented anchor of the present invention may be also a suture with biological material, as described in U.S. patent application Ser. No. 12/397,236, filed on Mar. 3, 2009, the disclosure of which is incorporated by reference in its entirety herein.

Strand 60 may be attached to the anchor body 50 by a connecting region disposed within distal end 59. The connecting region may be affixed to the distal end (for example, bonded to the distal end 59 and/or provided as a knot housed within the segment 55 of the distal end 59). In additional embodiments, at least a portion of strand 60 (preferably the whole length of strand 60) may be insert-molded directly into at least one of the segments 55 of the anchor 100 during the manufacturing process.

Segmented suture anchor 100 of the present invention may be employed for tissue repairs in a manner similar to that using a one-piece suture anchor. In an exemplary embodiment only, a pilot hole is created in bone by employing a punch or a drill, for example. After the pilot hole is created and the punch or drill is removed, segmented suture anchor 100 is loaded onto a driver (for example, a standard hand driver). One of two legs of suture is selected, and the selected suture leg is loaded through the eyelet 66 of the segmented suture anchor 100.

The segmented anchor is positioned on the driver, and the anchor with driver is inserted into the prepared pilot hole by hand. A mallet may be used to advance the implant into the hole. Once the segmented anchor is advanced into the pilot hole, the driver handle is pulled straight off the anchor. Additional anchors (segmented anchors and/or one-piece anchors) may be inserted dependent upon the size of the soft tissue defect. Suture passing and knot tying are carried out in the preferred fashion to secure attachment of soft tissue to bone.

A method of soft tissue repair with the segmented anchor 100 comprises the steps of: (i) providing a pilot hole through bone; (ii) providing, in the vicinity of the pilot hole, segmented suture anchor 100 with multiple body segments 55, at least two of the body segments 55 being connected by a material strand 60; (iii) attaching the suture anchor 100 to soft tissue to be attached to bone; and (iv) passing the suture anchor 100 through a straight or curved instrument, to insert the suture anchor 100 into the pilot hole.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of anchoring suture in bone, the method comprising the steps of:
providing a segmented suture anchor comprising a length of a flexible strand; and a plurality of individual body segments formed at least partially around and at least partially along the length of the flexible strand, the body segments having a tapered shape in the form of ribs terminating in a blunt, rounded distal end, the flexible strand forming an eyelet at a most proximal end of the suture anchor, the plurality of individual body segments being provided serially along the length of the flexible strand and in multiple pairs, the plurality of individual body segments being connected by the length of flexible strand, the segmented suture anchor further comprising a tapered drive head disposed on a most proximal body segment;
threading suture through the eyelet of the most proximal end of the segmented suture anchor;
loading the segmented suture anchor onto a driver by positioning the tapered drive head of the segmented suture anchor in a recess of the driver;
subsequently, inserting and passing the driver loaded with the segmented suture anchor arthroscopically through a substantially curved cannulated guide and installing the segmented suture anchor arthroscopically through the substantially curved cannulated guide; and
driving the suture anchor into a pilot hole in the bone.

2. The method of claim 1, wherein the bone is soft or cancellous bone.

3. The method of claim 1, wherein the suture anchor is formed by insert molding.

4. The method of claim 1, wherein the suture anchor further secures soft tissue to bone.

* * * * *